United States Patent [19]
Baker

[11] Patent Number: 6,077,485
[45] Date of Patent: Jun. 20, 2000

[54] STORAGE CONTAINER WITH FILTER

[75] Inventor: Terry L. Baker, Indianapolis, Ind.

[73] Assignee: Carr Metal Products, Inc., Indianapolis, Ind.

[21] Appl. No.: 09/086,948

[22] Filed: May 29, 1998

[51] Int. Cl.[7] .................................................. A61L 2/00
[52] U.S. Cl. .......................... 422/300; 206/363; 220/371; 422/297; 422/310
[58] Field of Search .................................... 422/297, 300, 422/310; 206/363–365; 220/300, 367.1, 371

[56] References Cited

U.S. PATENT DOCUMENTS

| | | | |
|---|---|---|---|
| 2,744,778 | 5/1956 | Coke | 292/250 |
| 2,893,771 | 7/1959 | Claud-Mantle | 292/113 |
| 3,338,387 | 8/1967 | Ferry | 206/1 |
| 4,241,833 | 12/1980 | Luebcke | 206/570 |
| 4,512,498 | 4/1985 | Leibinger | 220/371 |
| 4,551,311 | 11/1985 | Lorenz | 422/300 |
| 4,562,047 | 12/1985 | Sestak et al. | 422/300 |
| 4,617,178 | 10/1986 | Nichols | 422/310 |
| 4,661,326 | 4/1987 | Schainholz | 422/310 |
| 4,704,254 | 11/1987 | Nichols | 422/28 |
| 4,716,025 | 12/1987 | Nichols | 422/310 |
| 4,728,504 | 3/1988 | Nichols | 422/297 |
| 4,752,453 | 6/1988 | Nichols | 422/300 |
| 4,783,321 | 11/1988 | Spence | 422/300 |
| 4,900,519 | 2/1990 | Nichols | 422/292 |
| 4,915,913 | 4/1990 | Williams et al. | 422/119 |
| 4,915,918 | 4/1990 | Nichols | 422/292 |
| 5,050,778 | 9/1991 | Corrado et al. | 222/152 |
| 5,080,874 | 1/1992 | Nichols | 422/300 |
| 5,183,643 | 2/1993 | Nichols | 422/297 |
| 5,202,098 | 4/1993 | Nichols | 422/300 |
| 5,227,074 | 7/1993 | Nichols et al. | 210/767 |
| 5,257,839 | 11/1993 | Nielsen et al. | 292/113 |
| 5,324,489 | 6/1994 | Nichols et al. | 422/292 |
| 5,346,075 | 9/1994 | Nichols et al. | 211/60.1 |
| 5,474,738 | 12/1995 | Nichols et al. | 422/26 |
| 5,508,006 | 4/1996 | Gabele et al. | 422/119 |
| 5,630,507 | 5/1997 | Baker | 206/370 |

*Primary Examiner*—Krisanne Thornton
*Attorney, Agent, or Firm*—Woodard, Emhardt, Naughton, Moriarty & McNett Patent and Trademark Attorneys

[57] ABSTRACT

A storage container for autoclaving and storage of a medical instrument cassette includes a tray portion and a lid assembly which are securely closed together by means of a pair of spring-biased end latches. The lid assembly includes a lid gasket which is compressed by an outer lip of the tray portion and further includes a pair of low profile filter assemblies. Each filter assembly includes a retainer plate with an assembled edge seal, a paper filter, and a cover plate. The stack of these components creates a low profile design whose overall thickness in a direction normal to the surface of the lid is less than ⅜ of an inch. The cover plate is easily attached and removed for replacing the paper filter by means of keyhole-shaped apertures in the cover plate and lock studs assembled to the lid assembly which fit within the keyhole-shaped apertures. The two latch assemblies provide a visual indication as to whether the lid assembly is securely sealed onto the tray portion or is open.

18 Claims, 9 Drawing Sheets

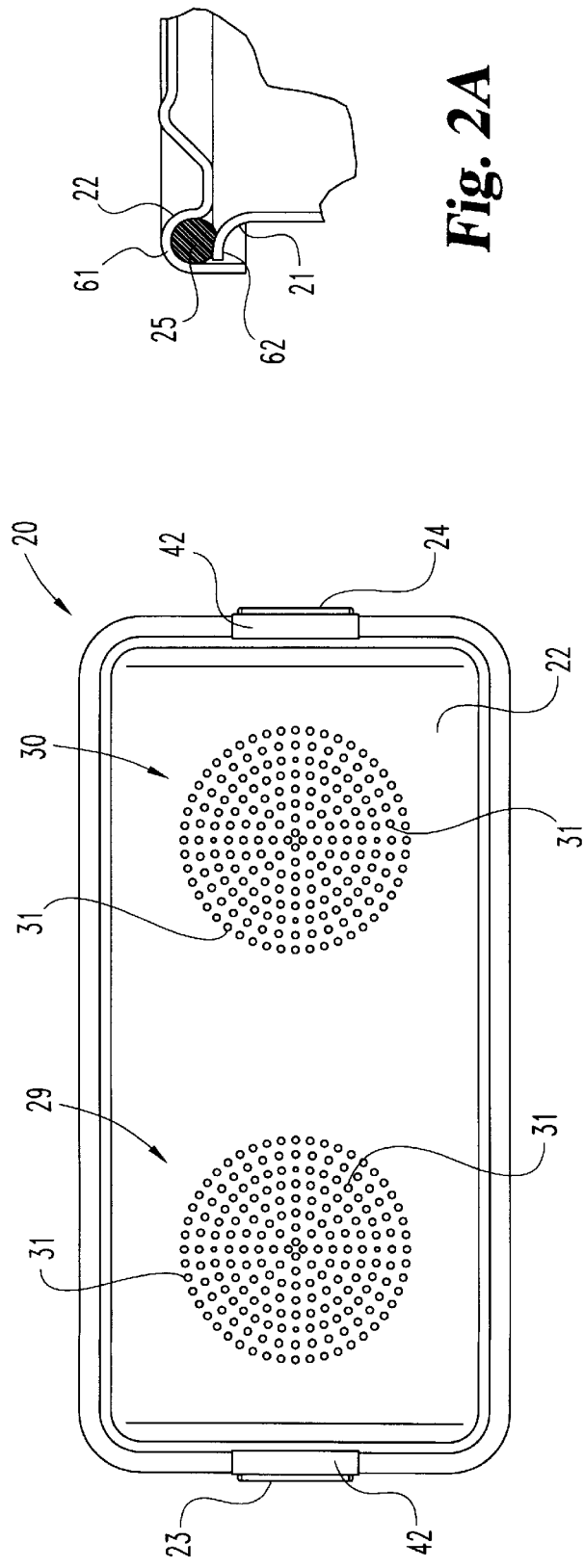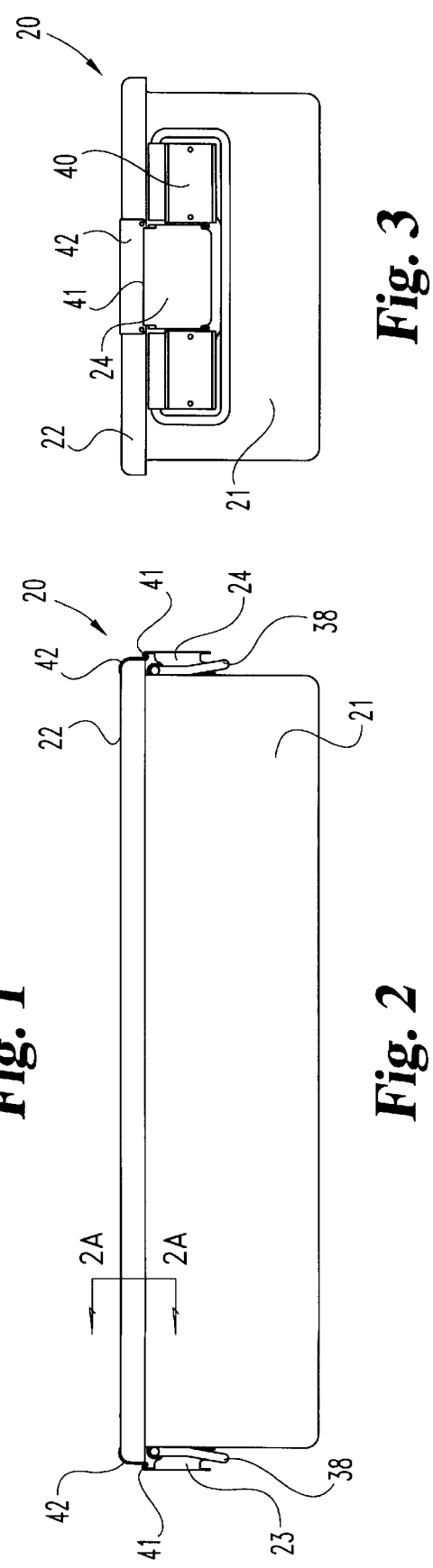

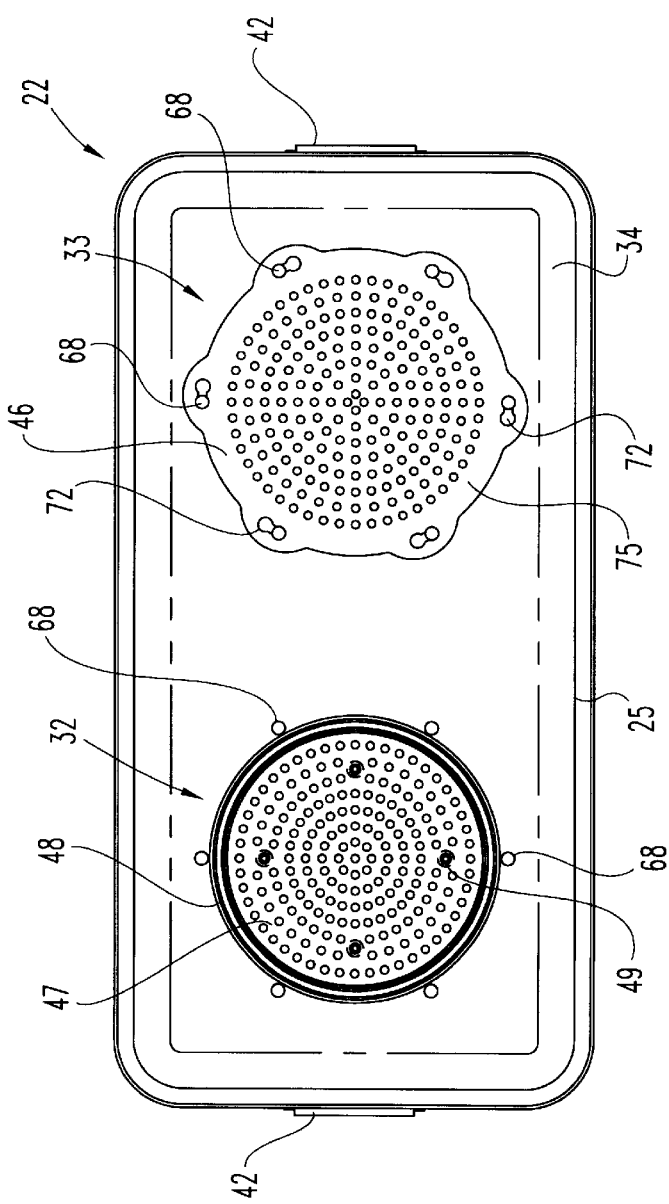
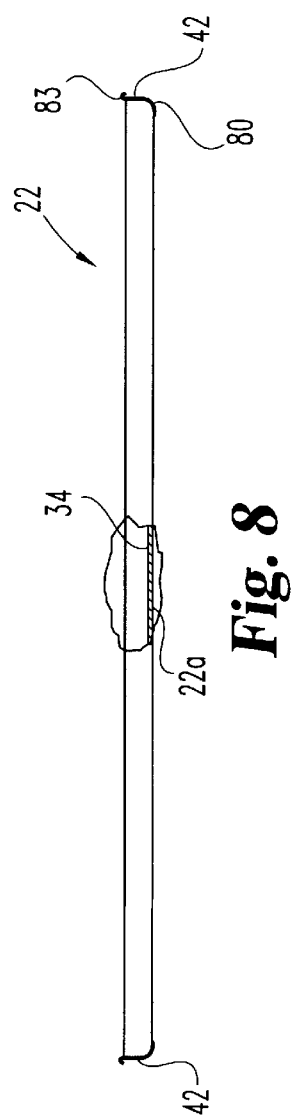
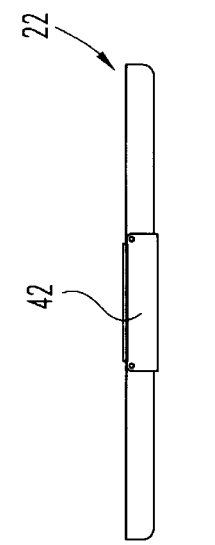

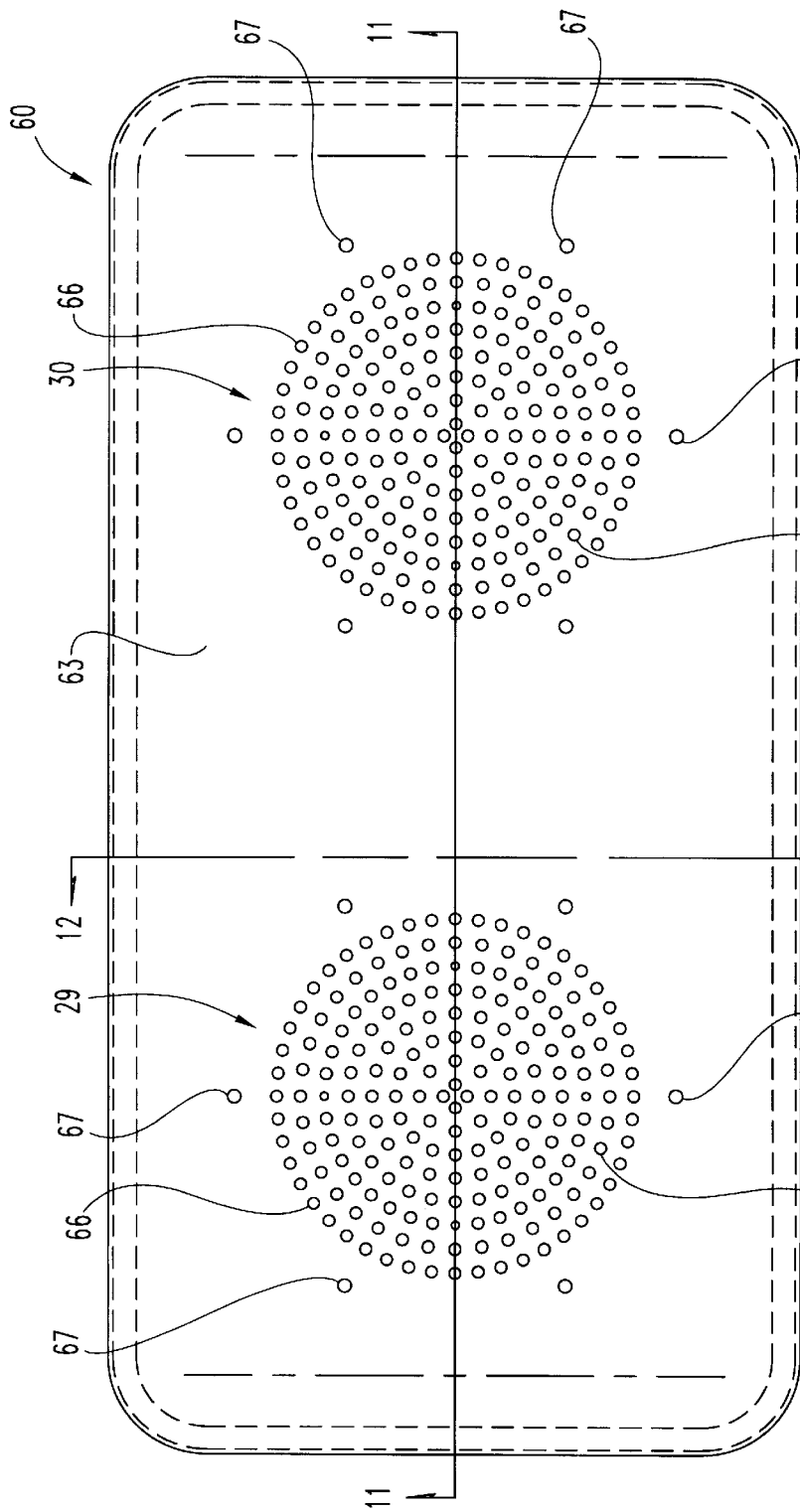
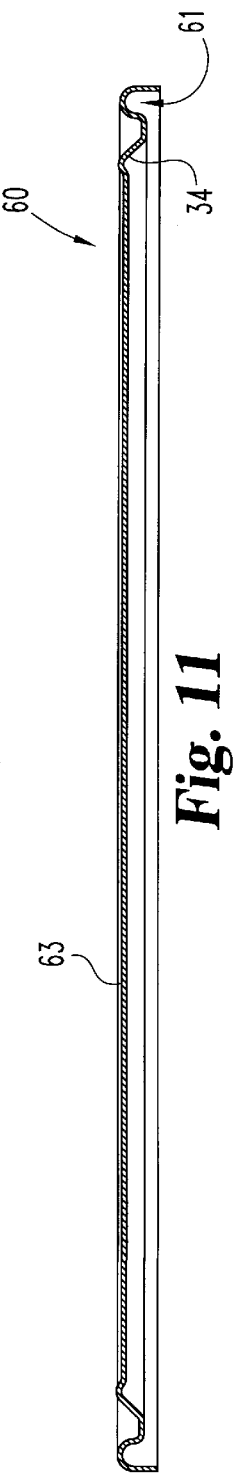
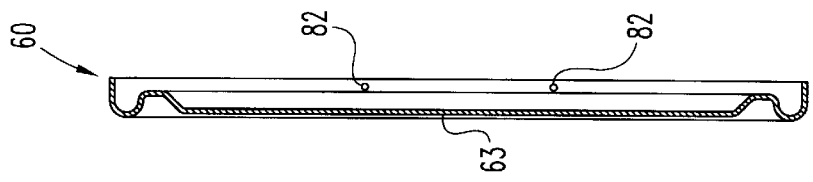

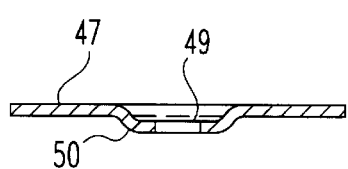
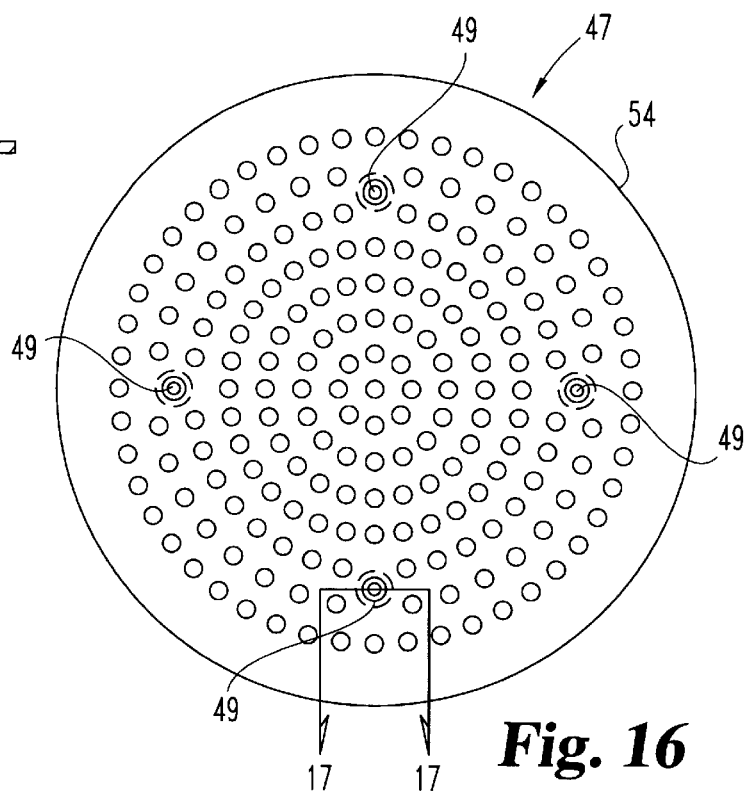
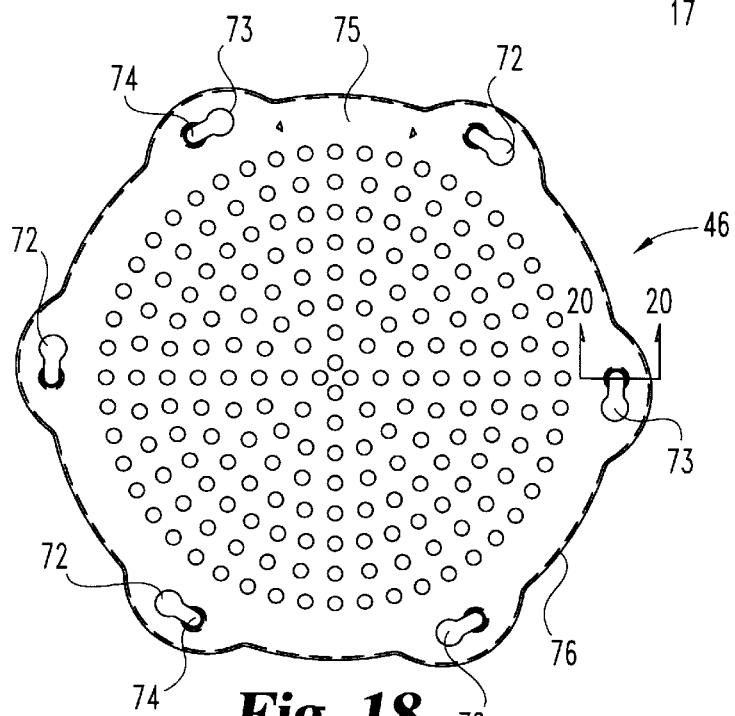
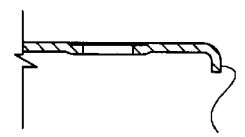
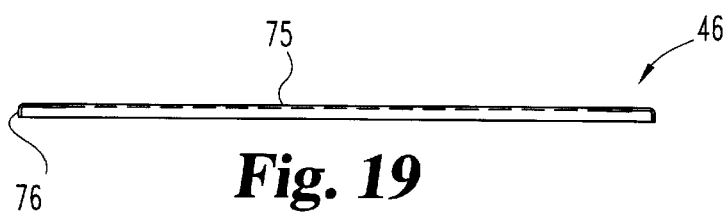

STORAGE CONTAINER WITH FILTER

BACKGROUND OF THE INVENTION

The present invention relates in general to an autoclavable storage container for a medical or dental instrument cassette. More specifically, the present invention relates to an autoclavable storage container which is constructed with a pair of filter panel assemblies located in a removable lid. The filter panel assemblies of the present invention are designed for a replaceable paper filter which permits the two-way flow of autoclave steriliant, while blocking the entry of bacteria and contaminants.

The sterilizing of an instrument cassette which includes medical and/or dental instruments and equipment is typically performed in one of two ways. In one approach, the loaded cassette is completely wrapped in a specific type of autoclave paper which allows the steriliant to flow through the paper and sterilize the instruments and the cassette generally. When the autoclaving procedure is completed, the wrapped cassette is stored until the instruments are required for a particular medical (or dental) procedure. The autoclave paper wrapping is then removed and discarded and the instruments in the cassette are readied for use.

In the other approach, the loaded cassette is placed within a larger storage container which is constructed and arranged with at least one filter panel assembly. The storage container includes a tray portion and an enclosing lid with a compression lid gasket which is used between the tray portion and the lid. The filter panel assembly which is typically located in the lid, or, alternatively, in one of the sidewalls of the tray portion, includes a replaceable paper filter or filter cartridge. Latches, some of which may be spring-biased, are typically used to clamp the lid and tray portion together.

While the wrapping approach is relatively simple to perform and relatively low cost from the perspective of front end fixed costs, the shelf life of the sterilized instrument cassette is relatively short, estimated to be a few weeks, maximum. Further, the wrapping paper represents a continuing or repeating cost and must be discarded after being unwrapped and removed from the cassette. Unwrapping and removal of the paper usually takes place in the operating room, and thus this discarding requirement could be viewed as a disadvantage or drawback of this approach.

With the approach using an enclosing storage container, there is a front end investment for the storage container, but the continuing costs of the replaceable paper filters is minimal. While cost is one consideration, the most significant advantage of this particular approach is the extended shelf life for the sterilized cassette, estimated to be several months.

Some of the concerns with existing storage container designs is that the filter panel assemblies are often bulky, complex, costly, and frequently extend inwardly from the lid into the hollow interior of the tray portion for a distance which is regarded as unacceptable. When the filter (panel) assembly extends some measureable distance into the hollow interior of the tray portion, it reduces the available storage volume inside the tray portion and could result in limiting the storage container to smaller cassettes. Another option for dealing with the loss or reduction in available interior space is to increase the depth of the tray portion which adds to the cost and increases the required storage space for the storage container due to the increased size. To the extent that storage space in the operating room for storage containers of the type disclosed herein is limited, then an increase in the size reduces the number of storage containers which can be stored in the operating room.

Other concerns with designs of the type disclosed herein include the integrity of any sealed interface around the filter paper to guarantee that the only path into the interior volume of the storage container is through the filter paper, not around the filter paper. Accordingly, it would be an improvement to existing designs to make the filter panel assembly with a lower profile in order to make the overall storage container more compact. In creating a filter panel assembly with such low profile, it would be an added improvement to provide a design which is easy to use and which establishes a secure seal around the replaceable paper filter. The present invention provides these various improvements. Another improvement provided by the present invention is the ease and convenience of replacing the paper filter.

Another feature of storage containers of the type disclosed herein is the use of spring-biased side or end latches which are used to draw the lid down tightly against the upper edge of the tray portion. The upper edge of the tray portion may include a sealing gasket or alternatively and preferably a sealing gasket is positioned within the lid. This gasket needs to be compressed for the desired seal between the tray portion and lid to be achieved. The present invention provides an improved sealing gasket (O-ring) design which expands in sealing area as it is compressed between the lid and the upper edge of the tray portion. It is also important to have latches which are easy to use and which visually indicate both the opened (unlatched) and the closed (latched) status of the latch. Such a visual indication aids the medical personnel in proper handling of the storage container and minimizes mishandling risks. The present invention also provides an improved latch design for use with storage containers of the type described herein.

SUMMARY OF THE INVENTION

A storage container for receipt of a medical instrument cassette for autoclaving and subsequent storage of the medical instrument cassette within the storage container until the medical instrument cassette is needed according to one embodiment of the present invention comprises a tray portion including a base and a plurality of surrounding sidewalls which cooperate to define a hollow interior space which is sized to receive therein a medical instrument cassette, a lid assembly, at least one latch assembly attached to the tray portion and cooperating with the lid assembly to clamp the lid assembly closed onto the tray portion and being movable to an unlatched condition wherein the lid assembly is removable from the tray portion and at least one filter assembly assembled into the storage container, the filter assembly including a removable cover plate which defines a plurality of cover apertures for an autoclave steriliant to flow through, the cover plate being positioned over a plurality of apertures for an autoclave steriliant to flow through and the filter assembly having a low profile design such that the overall thickness of the filter assembly is less than 3/8 inch.

One object of the present invention is to provide an autoclavable storage container for receipt and storage of a medical instrument cassette.

Related objects and advantages of the present invention will be apparent from the following description.

BRIEF DESCRIPTION OF THE DRAWINGS

FIG. 1 is a top plan view of a storage container according to a typical embodiment of the present invention.

FIG. 2 is a front elevational view of the FIG. 1 storage container.

FIG. 2A is a partial, side elevational view in full section of the FIG. 1 storage container as viewed along lines 2A—2A in FIG. 2.

FIG. 3 is a side elevational view of the FIG. 1 storage container.

FIG. 7 is a bottom plan view of a lid assembly which comprises one component of the FIG. 1 storage container.

FIG. 8 is a front elevational view of the FIG. 7 lid assembly.

FIG. 9 is a side elevational view of the FIG. 7 lid assembly.

FIG. 10 is a top plan view of the starting lid utilized in the FIG. 7 lid assembly.

FIG. 11 is a front elevational view in full section of the FIG. 10 lid as viewed along lines 11—11-in FIG. 10.

FIG. 12 is a side elevational view in full section of the FIG. 10 lid as viewed along lines 12—12 in FIG. 10.

FIG. 16 is a top plan view of a retainer plate which comprises one component of the filter assembly which is assembled into the FIG. 7 lid assembly.

FIG. 17 is a partial, front elevational view in full section of the FIG. 16 retainer plate as viewed along lines 17—17 in FIG. 16.

FIG. 18 is a top plan view of a cover plate which comprises one component of the filter assembly which is assembled into the FIG. 7 lid assembly.

FIG. 19 is a front elevational view of the FIG. 18 cover plate.

FIG. 20 is a partial, side elevational view in full section of the FIG. 18 cover plate as viewed along lines 20—20 in FIG. 18.

DESCRIPTION OF THE PREFERRED EMBODIMENT

Figure 4:
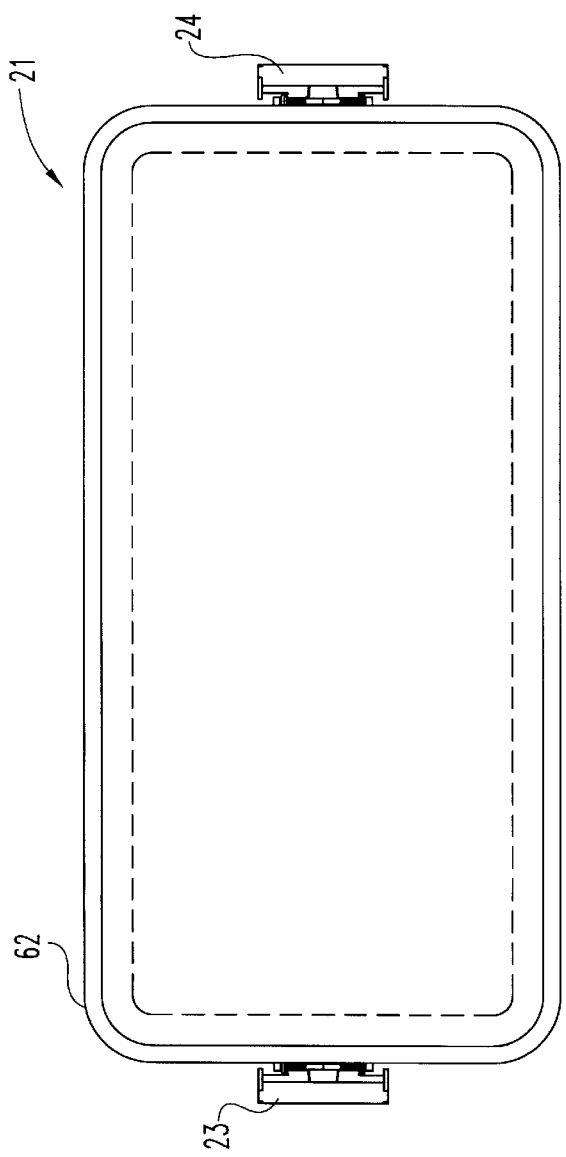
FIG. 4 is a top plan view of a tray portion comprising one component of the FIG. 1 storage container according to a typical embodiment of the present invention.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Referring to FIGS. 1, 2, and 3, there is illustrated a storage container 20 designed for receipt of an instrument cassette (either medical or dental) for autoclaving and longterm storage. Container 20 includes a tray portion 21, lid assembly 22, and a pair of end latch assemblies 23 and 24. The illustrations of FIGS. 1, 2, and 3 show the storage container 20 in its closed condition with both end latch assemblies 23 and 24 in a latched (i.e., closed) condition. In this condition the two latch assemblies 23 and 24 pull down on the lid assembly so as to compress the lid gasket 25 (see FIG. 2A) and create a sealed interior volume within container 20. The lid assembly includes two substantially identical circular patterns 29 and 30 of flow-through holes 31 for the flow of autoclave sterilant therethrough. These sterilant hole patterns 29 and 30 generally coincide with corresponding filter assemblies 32 and 33 which are attached to the inside surface 34 of the lid assembly 22 (see FIGS. 7 and 16–20).

With regarding to the clamping of lid gasket 25 between the lid assembly 22 and the tray portion 21, there are two important aspects. First, gasket 25, which extends uninterrupted completely around the periphery of the lid assembly and of the tray portion, is shaped in lateral section as a circle, thus having an overall O-ring configuration. Secondly, the outwardly turned lip 62 of the tray portion side wall panel (and end wall panel) has a radiused curvature in lateral section. The O-ring gasket 25 which is captured within outer channel 61 is thus allowed to spread out in contact area onto lip 62 as the lid assembly 22 and the tray portion 21 are drawn together by end latch assembles 23 and 24. The spreading out of gasket 25 increases the contact area and creates an improved sealed interface.

Figure 6:
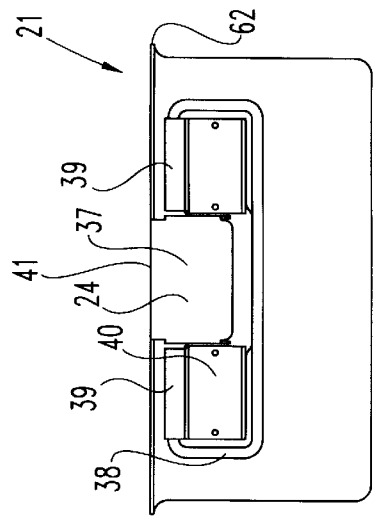
FIG. 6 is a side elevational view of the FIG. 4 tray portion.
Figure 5:
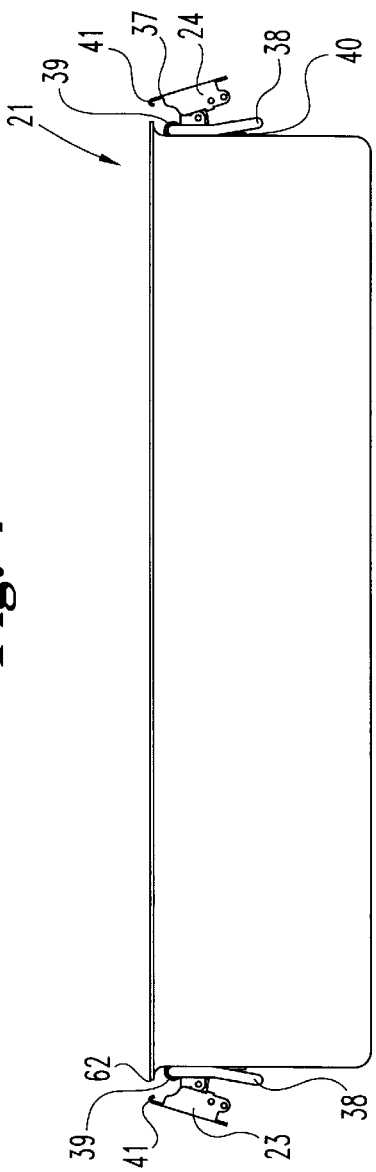
FIG. 5 is a front elevational view of the FIG. 4 tray portion.

Referring to FIGS. 4–6, the tray portion 21 with latch assemblies 23 and 24 attached is illustrated without the lid assembly 22. The two latch assemblies 23 and 24 are each illustrated in an open (unlatched) condition showing the latch catch 37 sprung open and spring-biased in this open orientation. The latch handles 38 are not spring-biased and accordingly simply lay against the corresponding side wall panel of the tray portion. Each handle is a partial rectangular loop with each of the facing free ends received within a corresponding pivot or hinge sleeve 39 which are part of the latch base 40. Each catch 37 includes an upper edge hook portion 41 which is used to interlock with and hook onto a corresponding latch strike 42. The two latch strikes 42 are securely attached to opposite ends of the lid assembly 22 (see FIGS. 8, 9, 30, and 31). While the tray portion 21 includes four side wall panels, two are actually end wall panels. The combination creates a generally rectangular shape, yet other shapes are contemplated within the scope of the present invention. The side wall and end wall panels in cooperation with the base or bottom wall panel define the hollow interior of the tray portion.

Figure 32:
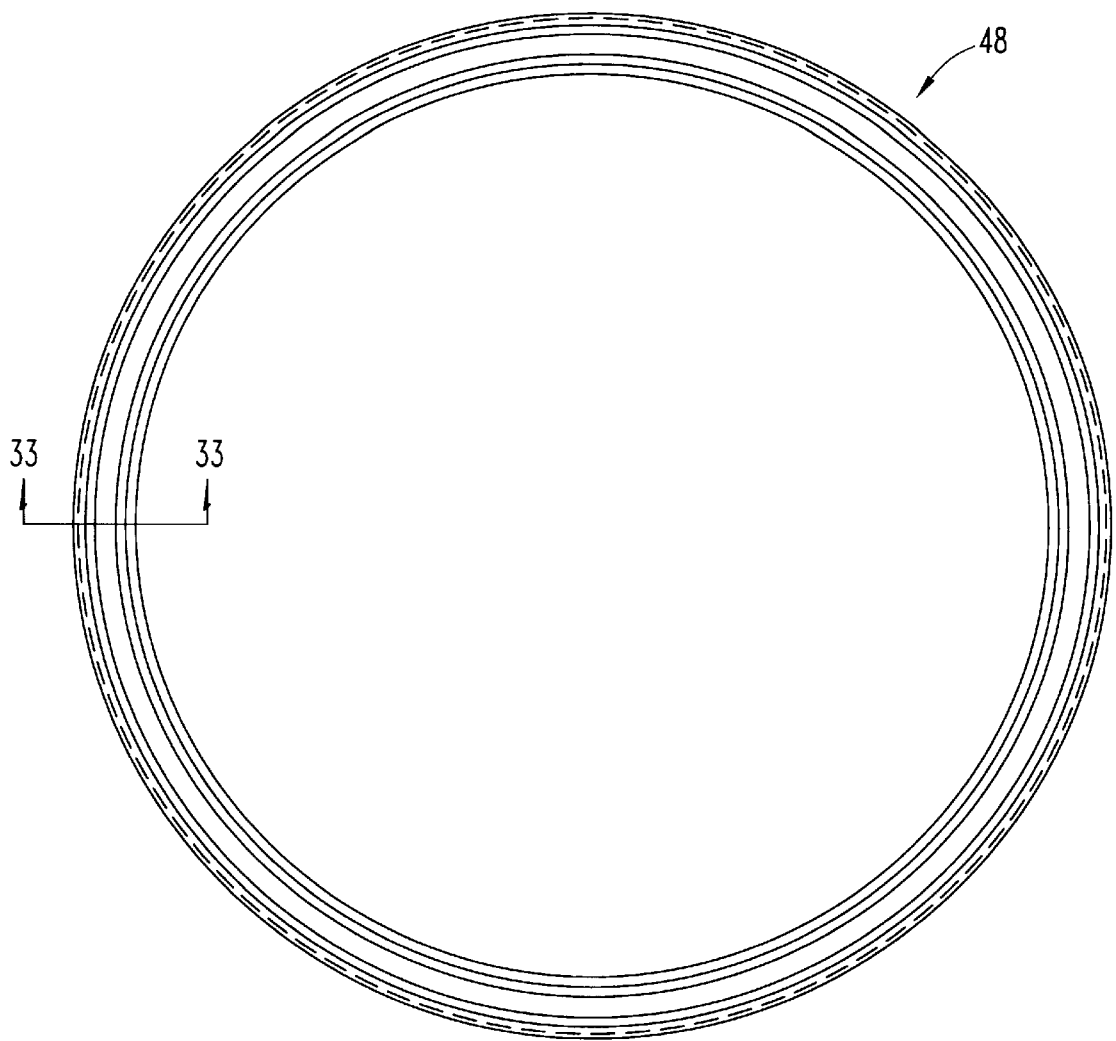
FIG. 32 is a top plan view of an edge seal which is designed to assemble to the FIG. 16 retainer plate.
Figure 33:
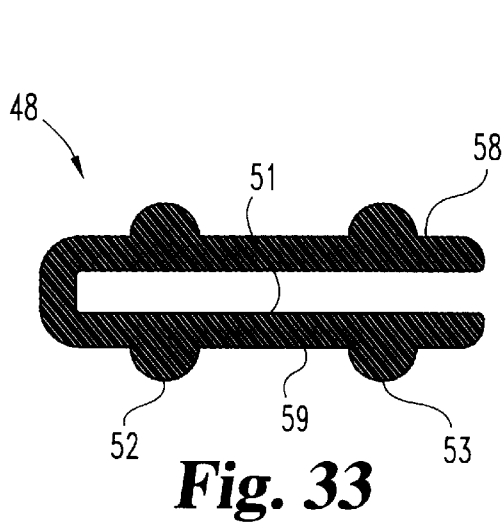
FIG. 33 is a partial, front elevational view in full section of the FIG. 32 edge seal as viewed along lines 33—33 in FIG. 2.

Referring more particularly to FIGS. 7, 8, and 9, the lid assembly 22 is illustrated in greater detail. Lid assembly 22 has a top panel 22a which includes the two filter assemblies 32 and 33, noting that the cover plate 46 (see FIGS. 18, 19, and 20) has been removed from assembly 32 for drawing clarity. The removal of cover plate 46 from filter assembly 32 allows the retainer plate 47 (see FIGS. 16 and 17) and edge seal 48 (see FIGS. 32 and 33) to be illustrated. Also note that the circular panel of filter paper which is captured between plates 46 and 47 as part of the completed filter assembly has been removed so that the features of plate 47 and edge seal 48 can be illustrated. The lid assembly has a generally rectangular shape which coincides with the shape of the tray portion.

As would be understood from a careful review of the drawings, the retainer plate 47 is attached to the inside surface 34 of lid assembly 22 at four (4) locations coinciding with holes 49. Plate 47 is a substantially flat, relatively thin (0.040 inches) disk of aluminum with an offset portion 50 surrounding each hole 49. These offset portions 50 provide a recessed pocket for the attaching hardware such as a rivet to remain flush with or below the surface of plate 47. Portions 50 also cause a slight spacing (0.057 inches) between the remainder of plate 47 and inside surface 34. This clearance space is completely filled in by the thickness of edge seal 48. One relevant thickness dimension of seal 48 is from the lower slot surface 51 to the outer (lowermost) edge of annular ribs 52 and 53. This dimension is approximately 0.062 inches which ensures that there will be contact by ribs 52 and 53 against surface 34. The slotted design of seal 48 and its circular shape enables it to fit onto and around the outer edge 54 of plate 47. The outside diameter of plate 47 measures approximately 6.75 inches which the inside diameter of seal 48 measures approximately 6.0 inches. These dimensions mean that there will be approximately ⅜ of an inch overlap of the walls (i.e., sides) 58 and 59 of seal 48 on the peripheral edge area of plate 47.

Figure 34:
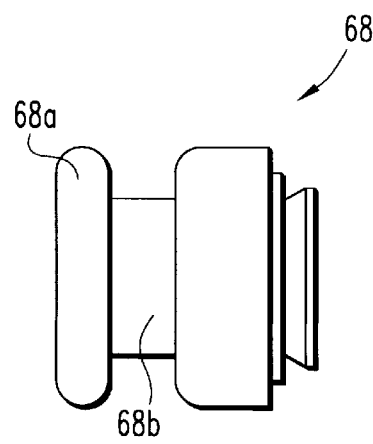
FIG. 34 is a side elevational view of a lock stud which comprises one portion of the FIG. 7 lid assembly according to the present invention.

The sheet metal (aluminum) lid 60 of lid assembly 22 (see FIGS. 10–12) is a generally rectangular, unitary member which is formed with specific edge contouring for the desired fit with the tray portion 21. The outer channel 61 which extends completely around lid 60 (including both ends, both sides, and the rounded corners) receives lid gasket 25. Adhesive may be used to securely seat gasket 25 in channel 61. When the lid assembly 22 is placed on the tray portion 21, the outwardly turned lip 62 fits up against the lid gasket 25. When the two latch assemblies 23 and 24 are properly hooked onto the corresponding latch strikes 42 and the latches are snapped closed, the lid gasket 25 is compressed by the tray portion lip 62 into a tightly sealed condition. The top surface 63 of top panel 22a is substantially flat and includes the two virtually identical, circular hole patterns 29 and 30 which are used in a cooperative manner with the filter assemblies 32 and 33. Each hole pattern 29 and 30 includes approximately 196 small diameter holes 66 which provide a sterilant path into and out of the closed (sealed) interior of the tray portion 21. Surrounding each hole pattern 29 and 30 are six equally-spaced counterbored holes 67. These counterbored holes are each used to receive a lock stud 68 of the style illustrated in FIG. 34. These lock studs 68 which are securely attached to lid 60 via holes 67 are used to attach cover plates 46, one cover plate aligned with each hole pattern. Holes 49 are used to attach the retainer plate 47 (and edge seal 48) to the lid 60 by way of four of the equally-spaced holes in patterns 29 and 30. Here again, the pattern of holes in plate 47 is positioned and aligned with the holes in patterns 29 and 30 for the flow of sterilant.

The paper filter used in each filter assembly 32 and 33 has an outside diameter size of approximately 6.88 inches. The outside diameter size of edge seal 48 is approximately 6.81 inches. This means that the paper filter rests on top of the edge seal and is securely clamped around its peripheral edge against the top edge of seal 48 by means of cover plate 46.

With reference to FIGS. 18, 19, and 20, the details of cover plate 46 are illustrated. Each of the six keyhole apertures 72 are designed to receive a corresponding lock stud 68. At each location the enlarged head 68a of the lock stud 68 fits up through enlarged end 73 of the corresponding keyhole aperture 72 such that the undercut shoulder 68b is able to slide into narrow portion 74 when the cover plate is turned in a clockwise direction based upon the FIG. 18 orientation. It is to be noted that the surface 75 of cover pate 46 surrounding each enlarged end 73 has a slight depression as compared to the surface of cover plate 46 surrounding each narrow portion 74. Accordingly, as the undercut shoulder 68b slides into portion 74, the enlarged head 68a pushes down on the top surface 75 of the cover plate 46. In order for the underside of the enlarged head 68a to slide across the top surface 75 which is adjacent the keyhole aperture, the cover plate must be pushed down to provide clearance and this action compresses the edge seal 48. Further, the cover plate 46 has a downturned lip 76 which fits around and actually captures a majority of the outside diameter of edge seal 48.

Each filter assembly 32 and 33 includes a retainer plate 47, cover plate 46, edge seal 48, lock stud 68, a circular paper filter, and appropriate mounting hardware. The use of the edge seal creates a liquid-tight configuration whereby the only sterilant path into or out of the interior of the enclosed tray portion must pass through the filter paper. As should be understood from a careful review of the various drawing illustrations and the assembly of the components for each filter assembly, a low profile design is provided. While apertures are provided in the lid for the passage of autoclave sterilant, the thickness or accumulation of layers for each filter assembly includes the thickness of edge seal 48 which in the uncompressed state measures approximately 0.164 inches, the thickness of the paper filter which is negligible, and the thickness (0.036 inches) of the metal used for cover plate 46. The only other dimension which should likely be included is the thickness of the enlarged head 68a of lock stud 68. This measures approximately 0.062 inches, resulting in a combined thickness or depth of approximately 0.262 inches prior to any compression of the edge seal 48. With an approximate 0.012 inches of compression to seal 48, the low profile of each filter assembly 32 and 33 will be approximately ¼ of an inch in total accumulation. As used herein, the concept of "low profile" with regard to each of the two filter assemblies 32 and 33 means a total stack of dimensional thicknesses in a direction normal to the surface of the lid 60 of between ¼ and ⅜ of an inch.

In order to create a lid assembly 22 from a beginning lid 60, two filter assemblies 32 and 33 are added, the lid gasket 25 is assembled (and seated with adhesive), and two latch strikes 42 (see FIGS. 30 and 31) are attached. Each latch strike 42 is a metal bracket with a first curved portion 80 whose shape generally matches the curvature of the metal which creates outer channel 61. The two holes 81 in each strike 42 are aligned with the two holes 82 in each of the ends of the lid. Conventional mounting hardware is used to attach each strike to the lid. Each strike 42 further includes a hook portion 83 which cooperates with hook portion 41 of latch catch 37 in order to pull the lid assembly 22 down onto the tray portion as the two latches are snapped closed.

While the lid 60 has been selected in the preferred embodiment for the location of the two filter assemblies 32 and 33, other locations within storage container 20 are contemplated by the present invention. For example, a pattern of holes 66 and a cooperating filter assembly can be located in a side wall panel of the tray portion 21 in addition to being located in the top panel of the lid or in lieu of being located in the top panel of the lid. The base of the tray portion also provides a suitable location for a filter assembly in combination with a lid panel location or in combination with a side wall panel location. Further, the shape of the pattern of holes and the cooperating filter assembly can be something other than circular, such as square or rectangular, for example.

Figure 13:
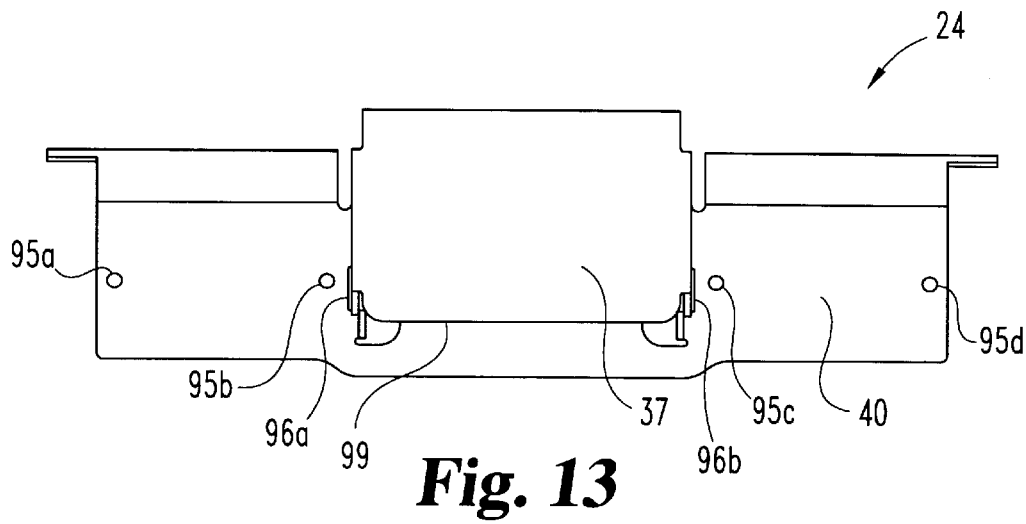
FIG. 13 is a front elevational view of one latch assembly which is utilized as part of the FIG. 1 storage container.
Figure 15:
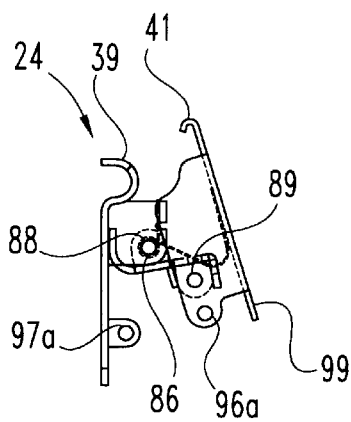
FIG. 15 is a diagrammatic, side elevational view of the FIG. 13 latch assembly.
Figure 14:
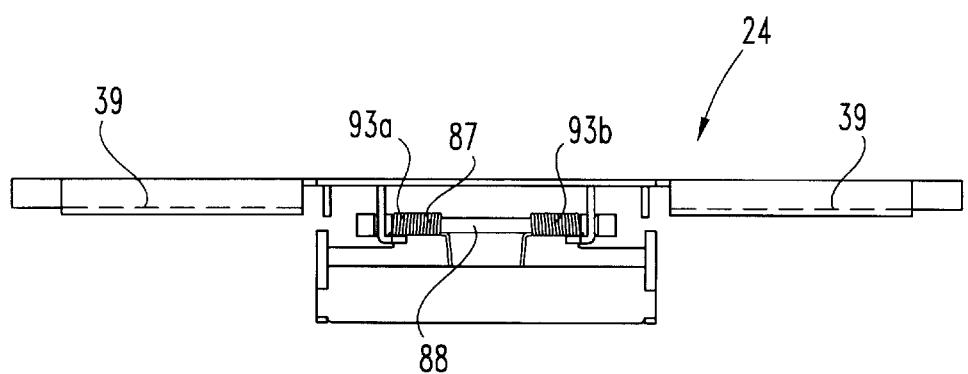
FIG. 14 is a top plan view of the FIG. 13 latch assembly.
Figure 21:
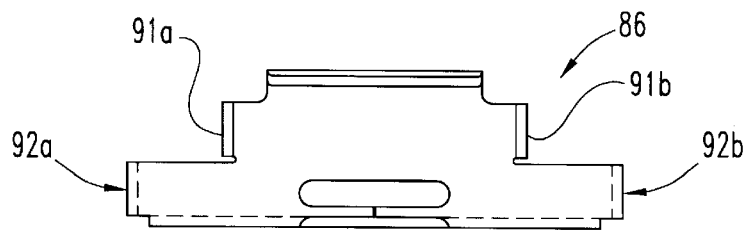
FIG. 21 is a top plan view of a pivot comprising one component of the FIG. 13 latch assembly.
Figure 23:
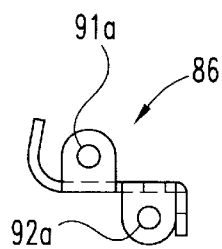
FIG. 23 is a side elevational view of the FIG. 21 pivot.
Figure 22:
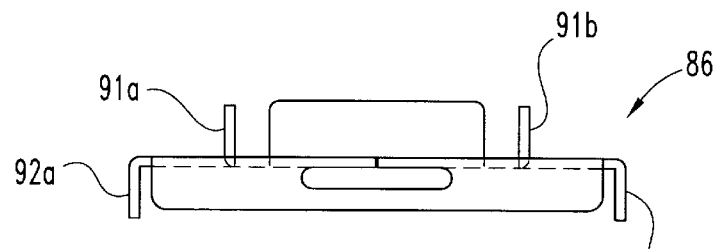
FIG. 22 is a front elevational view of the FIG. 21 pivot.
Figure 24:
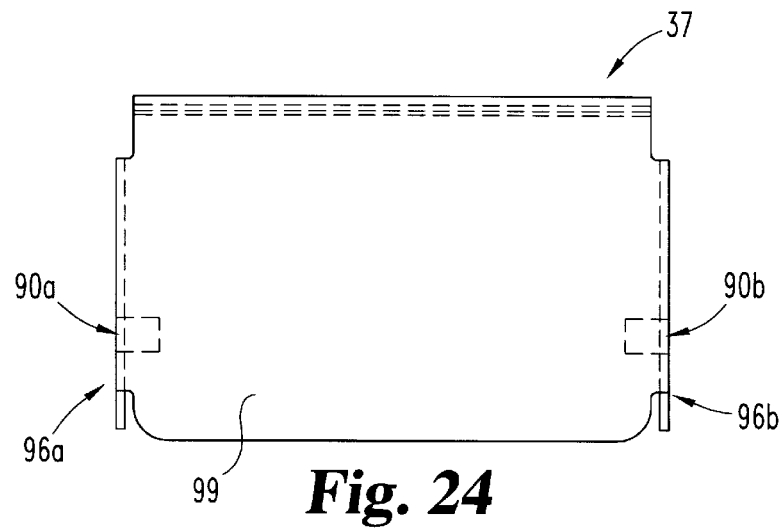
FIG. 24 is a front elevational view of a latch which comprises one portion of the FIG. 13 latch assembly.
Figure 26:
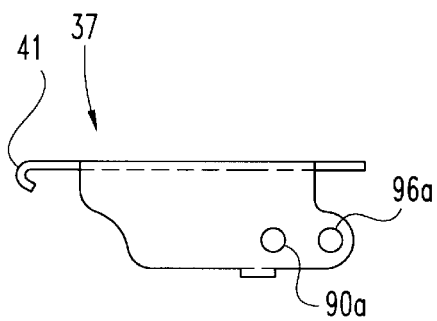
FIG. 26 is a side elevational view of the FIG. 24 latch.
Figure 25:
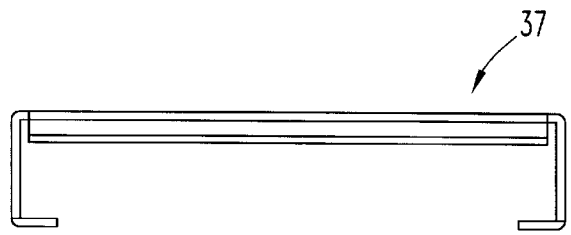
FIG. 25 is a bottom plan view of the FIG. 24 latch.
Figure 27:
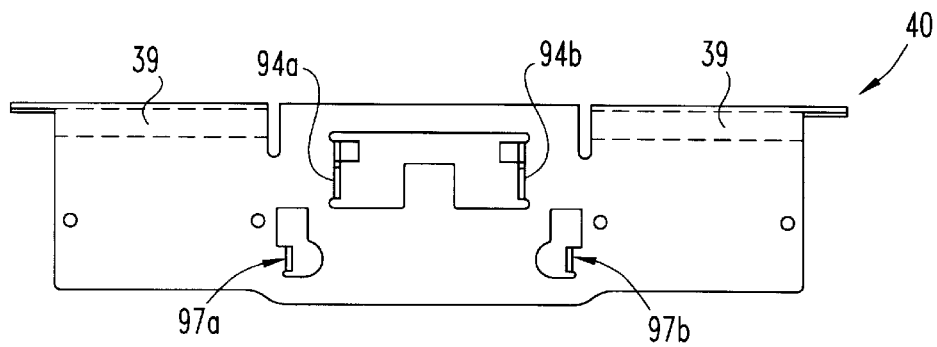
FIG. 27 is a front elevational view of a base comprising one portion of the FIG. 13 latch assembly.
Figure 28:
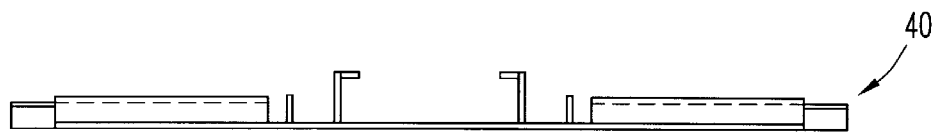
FIG. 28 is a bottom plan view of the FIG. 27 base.
Figure 30:
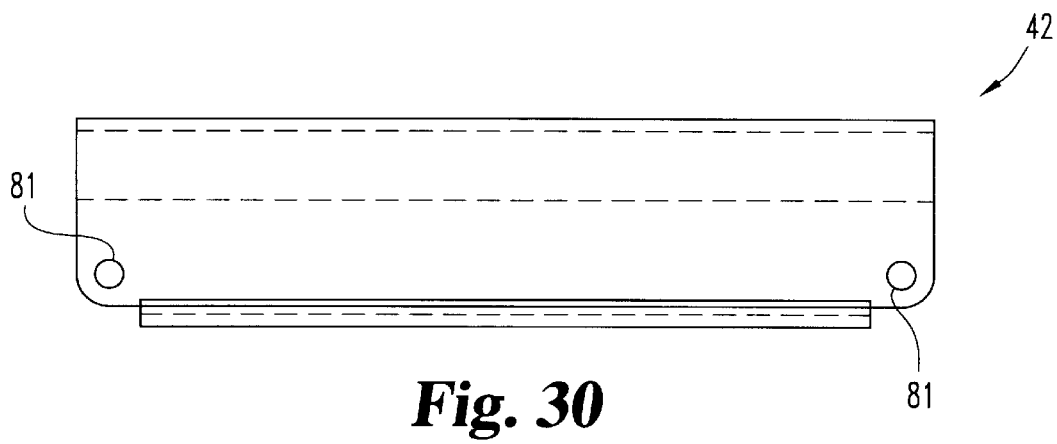
FIG. 30 is a front elevational view of a strike which is attached as part of the FIG. 7 lid assembly and cooperates with the FIG. 13 latch assembly.
Figure 29:
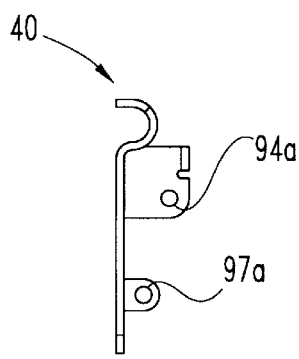
FIG. 29 is a side elevational view of the FIG. 26 base.
Figure 31:
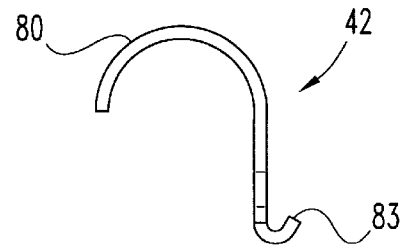
FIG. 31 is a side elevational view of the FIG. 30 strike.

With reference to FIGS. 13–15, one of the two latch assemblies 23 and 24 is illustrated in detail in an open condition. Latch assembly 24 is illustrated without handle 38 assembled. Latch assembly 24 includes latch catch 37, latch base 40, latch pivot 86, latch spring 87, spring pin 88, and hinge pin 89. The details of catch 37 are illustrated in FIGS. 24–26. The details of base 40 are illustrated in FIGS. 27–29. The details of pivot 86 are illustrated in FIGS. 21–23. In order to aid in an understanding of the latch assembly, FIG. 15 is diagrammatically illustrated in order to show the interfit and assembly of the various components.

With continued reference to FIGS. 13–15 and with supporting reference to the detailed drawings of FIGS. 21–29, it will be understood that the catch 37, base 40, and pivot 86 are all connected together by means of hinge pin 89 and spring pin 88. Pin 89 extends through holes 90*a* and 90*b* of catch 37, and through holes 92*a* and 92*b* of pivot 86. Spring pin 88 extends through the two coiled portions 93*a* and 93*b* of spring 87 and is received by holes 94*a* and 94*b* in base 40 and by holes 91*a* and 91*b* in pivot 86. As an option for the present invention, holes 96*a* and 96*b* in catch 37 can be connected to holes 97*a* and 97*b* in base 40 so as to lock each of the latch assemblies 23 and 24 in a closed condition. While a lock can be used, it is also possible to simply use a wire or cable tie.

Four clearance holes 95*a*–95*d* in base 40 provide a way for the base to be securely attached to one end wall of the tray portion. While virtually any type of conventional fastener or mounting hardware can be used, the preferred approach is to rivet the base 40 to the end wall of the tray portion. The attachment of the base to the tray portion causes the open side of the two sleeves 39 to be positioned against the tray portion, thereby enabling the free ends of the corresponding handle 38 to be captured and retained.

In operation, latch assemblies 23 and 24 are movable from a closed/latched condition or orientation (see FIGS. 1–3) to an open/unlatched condition (see FIGS. 4–6). The movement of each latch assembly 23 and 24 is controlled by the pivoting of catch 37 and the pivoting movement of latch pivot 86. Spring 87 maintains a constant spring biasing force on catch 37 so that in both the closed and opened conditions, the latch 37 is not free to wobble or change position simply by movement and handing of the tray portion. In order to release the hook portion 41 from the strike, the tongue 99 of the catch 37 is lifted (pivoted) out and up. A slight upward travel enabled by pivoting of pivot 86 disengages the hook portion from the strike. By then pulling outwardly and downwardly on the catch, the pivot 86 pivots outwardly and downwardly to the opened/unlatched condition of FIGS. 4–6. The foregoing procedure is reversed in order to return the latch and strike to their closed condition as illustrated in FIGS. 1–3.

By causing each latch assembly 23 and 24 to be somewhat static or stationary once it is either opened or closed, it is easy to tell the status of each latch assembly upon visual inspection. Due to the design of pivot 86 and its use as well as the spring biasing use of spring 87, medical personnel can readily tell by simple visual inspection the condition of the latch assembly and, in turn, the condition or status of the tray portion 21 and lid assembly 22. Accordingly there is little or no risk that the storage container will be handled by personnel believing, incorrectly, that the lid assembly is securely latched when it is not. This in turn reduces the risk of any mishandling or careless handling which might cause the contents of the storage container to be spilled. A further advantage of being able to visually ascertain the status of each latch assembly is that a storage container which is believed to hold a sterilized instrument cassette, when in fact it is no longer sterile due to open latch assemblies, will not be mistakenly used as sterile. If a storage container is withdrawn from storage and it is noticed that either of the two latch assemblies are in an opened condition, the medical personnel will be immediately alerted to the fact that what was believed to be a sterile instrument cassette may in fact not be sterile any longer.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A storage container for receipt of a medical instrument cassette for autoclaving and subsequent storage of the medical instrument cassette within the storage container until the medical instrument cassette is needed, said storage container comprising:

a tray portion including a base and a plurality of surrounding side walls which cooperate to define a hollow interior space which is sized to receive therein a medical instrument cassette;

a lid assembly including a plurality of lid apertures for an autoclave sterilant to flow through;

at least one latch assembly attached to the tray portion and cooperating with said lid assembly to clamp the lid assembly closed onto the tray portion and being movable to an unlatched condition wherein said lid assembly is removable from said tray portion; and at least one filter assembly assembled into said lid assembly, said at least one filter assembly including a removable cover plate defining a plurality of cover apertures for an autoclave sterilant to flow through, said cover plate being positioned over said lid apertures, said at least one filter assembly having a low profile design such that the overall thickness of said at least one filter assembly, prior to being assembled into said lid assembly, is less than $\frac{3}{8}$ of an inch.

2. The storage container of claim 1 wherein said at least one latch assembly includes a catch, a base, a pivot member, a spring, a spring pin, and a hinge pin.

3. The storage container of claim 2 which further includes a strike member attached to said lid assembly, said strike member cooperating with said at least one latch assembly for the closing of said lid assembly onto the tray portion.

4. The storage container of claim 3 which further includes a plurality of lock studs attached to said lid assembly, said cover plate being constructed and arranged to assemble onto said plurality of lock studs.

5. A storage container for receipt of a medical instrument cassette for autoclaving and subsequent storage of the medical instrument cassette within the storage container until the medical instrument cassette is needed, said storage container comprising:

a tray portion including a base panel and a plurality of surrounding side wall panels which cooperate to define a hollow interior space which is sized to receive therein a medical instrument cassette;

a lid assembly including a top panel;

at least one latch assembly attached to the tray portion and cooperating with said lid assembly to clamp the lid assembly closed onto the tray portion and being movable to an unlatched condition wherein said lid assembly is removable from said tray portion; and at least one filter assembly assembled into one of said panels, said at least one filter assembly including a removable cover plate defining a plurality of cover apertures for an autoclave sterilant to flow through, said cover plate being positioned over a plurality of apertures defined by said one of said panels for an autoclave sterilant to flow through, said at least one filter assembly having a low profile design such that the overall thickness of said at least one filter assembly, prior to being assembled into one of said panels, is less than ⅜ of an inch.

6. The storage container of claim 5 wherein said at least one latch assembly includes a catch, a base, a pivot member, a spring, a spring pin, and a hinge pin.

7. The storage container of claim 6 which further includes a strike member attached to said lid assembly, said strike member cooperating with said at least one latch assembly for the closing of said lid assembly onto the tray portion.

8. The storage container of claim 7 which further includes a plurality of lock studs attached to said lid assembly, said cover plate being constructed and arranged to assemble onto said plurality of lock studs.

9. A storage container for receipt of a medical instrument cassette for autoclaving and subsequent storage of the medical instrument cassette within the storage container until the medical instrument cassette is needed, said storage container comprising:

a tray portion including a base and a plurality of surrounding side walls which cooperate to define a hollow interior space which is sized to receive therein a medical instrument cassette;

a lid assembly including a plurality of lid apertures for an autoclave sterilant to flow through;

at least one latch assembly attached to the tray portion and cooperating with said lid assembly to clamp the lid assembly closed onto the tray portion; and at least one filter assembly assembled into said lid assembly, said at least one filter assembly including a removable cover plate defining a plurality of cover apertures for an autoclave sterilant to flow through, said cover plate being positioned over said lid apertures, said at least one filter assembly having a low profile design such that the overall thickness of said at least one filter assembly, as assembled into said lid assembly, is less than 9/32 of an inch.

10. A storage container for receipt of a medical instrument cassette for autoclaving and subsequent storage of the medical instrument cassette within the storage container until the medical instrument cassette is needed, said storage container comprising:

a tray portion including a base panel and a plurality of surrounding side wall panels which cooperate to define a hollow interior space which is sized to receive therein a medical instrument cassette;

a lid assembly including a top panel;

at least one latch assembly attached to the tray portion and cooperating with said lid assembly to clamp the lid assembly closed onto the tray portion; and at least one filter assembly assembled into one of said panels, said at least one filter assembly including a removable cover plate defining a plurality of cover apertures for an autoclave sterilant to flow through, said cover plate being positioned over a plurality of apertures defined by said one of said panels for an autoclave sterilant to flow through, said at least one filter assembly having a low profile design such that the overall thickness of said at least one filter assembly, as assembled into one of said panels, is less than 9/32 of an inch.

11. A storage container for receipt of a medical instrument cassette for autoclaving and subsequent storage of the medical instrument cassette within the storage container until the medical instrument cassette is needed, said storage container comprising:

a tray portion including a base and a plurality of surrounding side walls which cooperate to define a hollow interior space which is sized to receive therein a medical instrument cassette;

a lid assembly including a plurality of lid apertures for an autoclave sterilant to flow through;

at least one latch assembly attached to the tray portion and cooperating with said lid assembly to clamp the lid assembly closed onto the tray portion; and at least one filter assembly assembled into said lid assembly, said at least one filter assembly including a removable cover plate defining a plurality of cover apertures for an autoclave sterilant to flow through, said cover plate being positioned over said lid apertures, said at least one filter assembly having a low profile design such that the overall thickness of said at least one filter assembly, prior to being assembled into said lid assembly, is less than ⅜ of an inch.

12. A storage container for receipt of a medical instrument cassette for autoclaving and subsequent storage of the medical instrument cassette within the storage container until the medical instrument cassette is needed, said storage container comprising:

a tray portion including a base panel and a plurality of surrounding side wall panels which cooperate to define a hollow interior space which is sized to receive therein a medical instrument cassette;

a lid assembly including a top panel;

at least one latch assembly attached to the tray portion and cooperating with said lid assembly to clamp the lid assembly closed onto the tray portion; and at least one filter assembly assembled into one of said panels, said at least one filter assembly including a removable cover plate defining a plurality of cover apertures for an autoclave sterilant to flow through, said cover plate being positioned over a plurality of apertures defined by said one of said panels for an autoclave sterilant to flow through, said at least one filter assembly having a low profile design such that the overall thickness of said at least one filter assembly, prior to being assembled into one of said panels, is less than 3/8 of an inch.

13. A storage container for receipt of a medical instrument cassette for autoclaving and subsequent storage of the medical instrument cassette within the storage container until the medical instrument cassette is needed, said storage container comprising:

a tray portion including a base and a plurality of surrounding side walls which cooperate to define a hollow interior space which is sized to receive therein a medical instrument cassette;

a lid assembly including a plurality of lid apertures for an autoclave sterilant to flow through and a plurality of studs, each stud having an enlarged head and an undercut shoulder;

at least one latch assembly attached to the tray portion and cooperating with said lid assembly to clamp the lid assembly closed onto the tray portion; and at least one filter assembly assembled into said lid assembly, said at least one filter assembly including a removable cover plate defining a plurality of cover apertures for an autoclave sterilant to flow through, said cover plate further including a plurality of keyhole apertures, each keyhole aperture of said plurality being constructed and arranged for receiving one of said studs.

14. The storage container of claim 13 wherein said filter assembly includes a retainer plate and an edge seal assembled to said retainer plate for sealing around said plurality of lid apertures.

15. The storage container of claim 14 wherein said removable cover plate is constructed and arranged to rotate relative to said studs such that said cover plate assembles to said lid assembly by clockwise rotation and is removable by counterclockwise rotation, said cover plate further including a portion surrounding each of said plurality of keyhole apertures and having one area around each of said plurality of keyhole apertures with a slight depression such that clockwise rotation of said cover plate creates a compressive force on said edge seal.

16. A storage container for receipt of a medical instrument cassette for autoclaving and subsequent storage of the medical instrument cassette within the storage container until the medical instrument cassette is needed, said storage container comprising:

a tray portion including a base and a plurality of surrounding side walls which cooperate to define a hollow interior space which is sized to receive therein a medical instrument cassette;

a lid assembly including a plurality of lid apertures for an autoclave sterilant to flow through;

at least one latch assembly attached to the tray portion and cooperating with said lid assembly to clamp the lid assembly closed onto the tray portion; and at least one filter assembly assembled into said lid assembly, said at least one filter assembly including a retainer plate, an edge seal assembled to said retainer plate, a filter element and a removable cover plate defining a plurality of cover apertures for an autoclave sterilant to flow through, said cover plate further including a down-turned peripheral lip which surrounds said filter element and captures a portion of said edge seal.

17. A storage container for receipt of a medical instrument cassette for autoclaving and subsequent storage of the medical instrument cassette within the storage container until the medical instrument cassette is needed, said storage container comprising:

a tray portion including a base and a plurality of surrounding side walls which cooperate to define a hollow interior space which is sized to receive therein a medical instrument cassette, each of said plurality of surrounding sidewalls including a curved upper lip which extends away from said hollow interior space;

a lid assembly including a plurality of lid apertures for an autoclave sterilant to flow through, said lid assembly further including an outer channel which is positioned above said curved upper lip when said lid assembly is attached to the tray portion, said lid assembly further including a lid gasket having a lateral cross sectional shape which is circular, said lid gasket being positioned within said outer channel and in contact with said curved upper lip when said lid assembly is attached to the tray portion.

18. The storage container of claim 17 which further includes at least one filter assembly assembled into said lid assembly, said at least one filter assembly including a removable cover plate defining a plurality of cover apertures for an autoclave sterilant to flow through, said cover plate being positioned over said lid apertures, said at least one filter assembly having a low profile design such that the overall thickness of said at least one filter assembly, as assembled into one of said panels, is less than 9/32 of an inch.

* * * * *